United States Patent [19]
Chanoch et al.

[11] Patent Number: 5,542,760
[45] Date of Patent: Aug. 6, 1996

[54] SYRINGE FILLER FOR MIXING INSULINS

[75] Inventors: Lawrence H. Chanoch, Mahwah; John B. Wilson, Wanaque, both of N.J.

[73] Assignee: Becton Dickinson and Company, Franklin Lakes, N.J.

[21] Appl. No.: 534,152

[22] Filed: Sep. 26, 1995

[51] Int. Cl.⁶ .................... B01F 15/04; A61M 37/00
[52] U.S. Cl. .................. 366/160.4; 222/135; 222/144.5; 222/390; 366/162.3; 604/56; 604/82; 604/232
[58] Field of Search .............. 366/150.1, 152.1, 366/152.2, 160.1, 160.2, 160.4, 162.3, 162.1, 348, 349; 222/135, 144.5, 390; 604/56, 82, 232, 57

[56] References Cited

U.S. PATENT DOCUMENTS

| | | | |
|---|---|---|---|
| 4,668,097 | 5/1987 | Nygren | 366/162.3 |
| 4,850,516 | 7/1989 | Seager | 222/390 |
| 5,116,315 | 5/1992 | Capozzi | 608/82 |
| 5,169,029 | 12/1992 | Behar | 222/135 |
| 5,253,785 | 10/1993 | Haber | 222/135 |
| 5,348,392 | 9/1994 | Bouquet | 366/162.3 |
| 5,425,580 | 6/1995 | Beller | 604/82 |
| 5,484,410 | 1/1996 | Kriesel | 604/82 |

*Primary Examiner*—Robert W. Jenkins
*Attorney, Agent, or Firm*—Alan W. Fiedler

[57] ABSTRACT

A device and method for filling a conventional disposable plastic syringe with a mixture of insulins. The mixing device includes a pair of disposable cartridge assemblies each containing a different type of medication to be mixed in the syringe and a pair of medication dispensing mechanisms for dispensing the medication out of a respective cartridge. Each dispensing mechanism permits one to specify the dose of medication to be dispensed and drives a plunger into its respective cartridge a specific distance based on the specified dose. The mixing device also includes a syringe holder assembly that holds a syringe until a mixed dose of medication must be dispensed and provides proper alignment of the cannula of the syringe with each cartridge assembly during mixing.

8 Claims, 9 Drawing Sheets

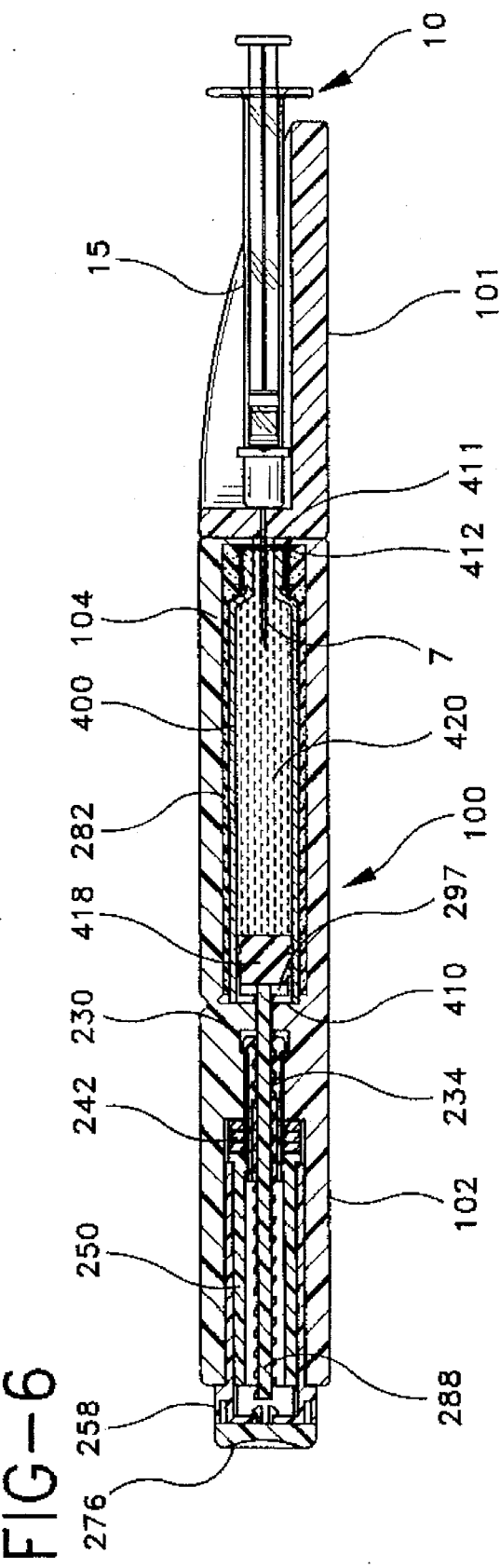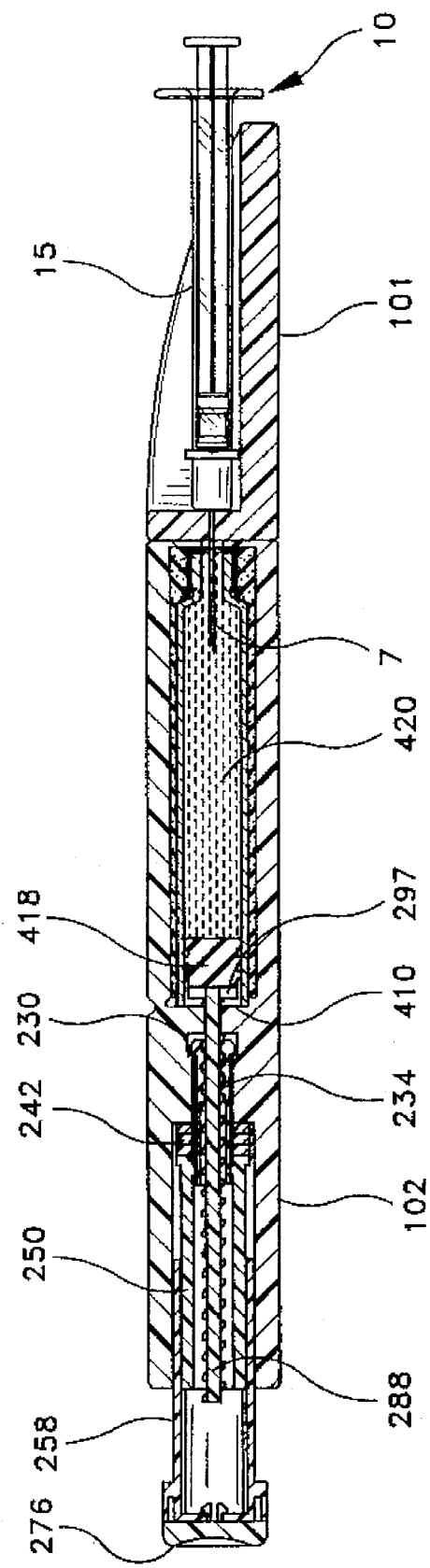

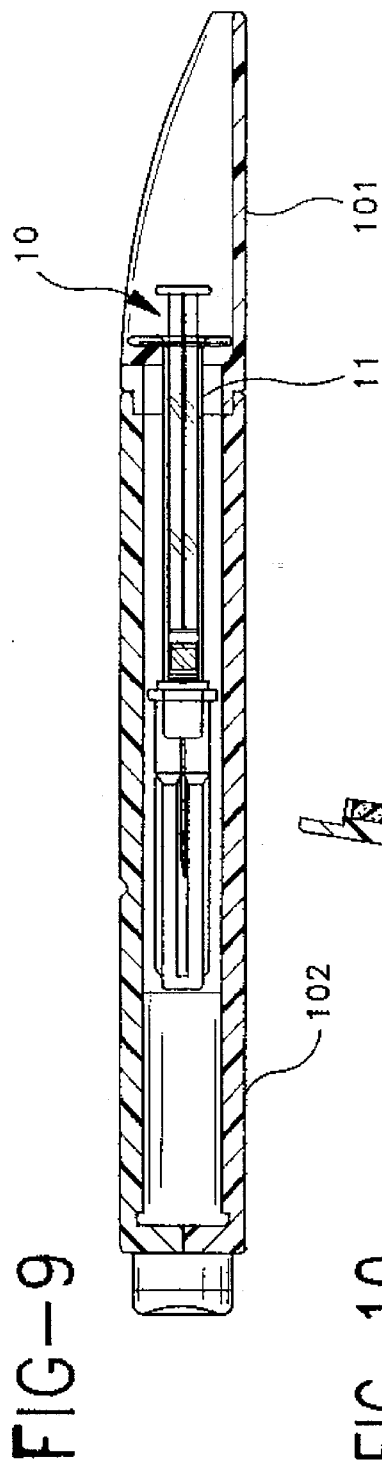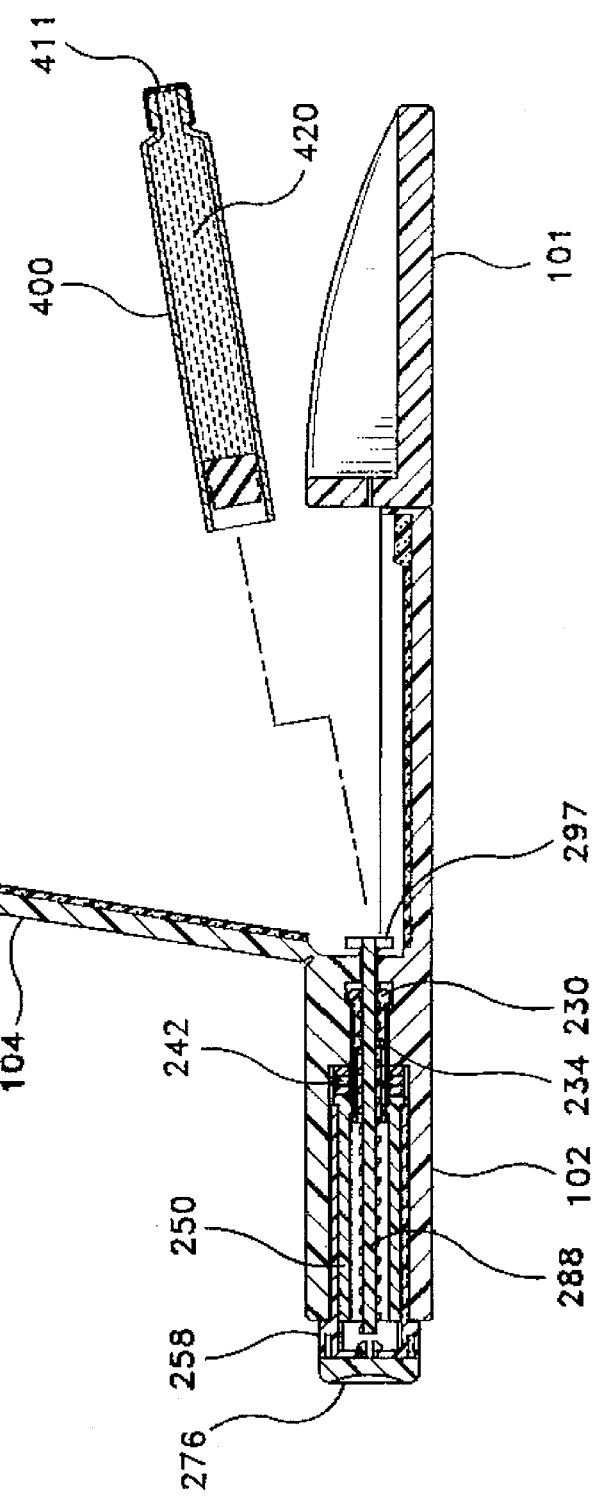
FIG-9
FIG-10

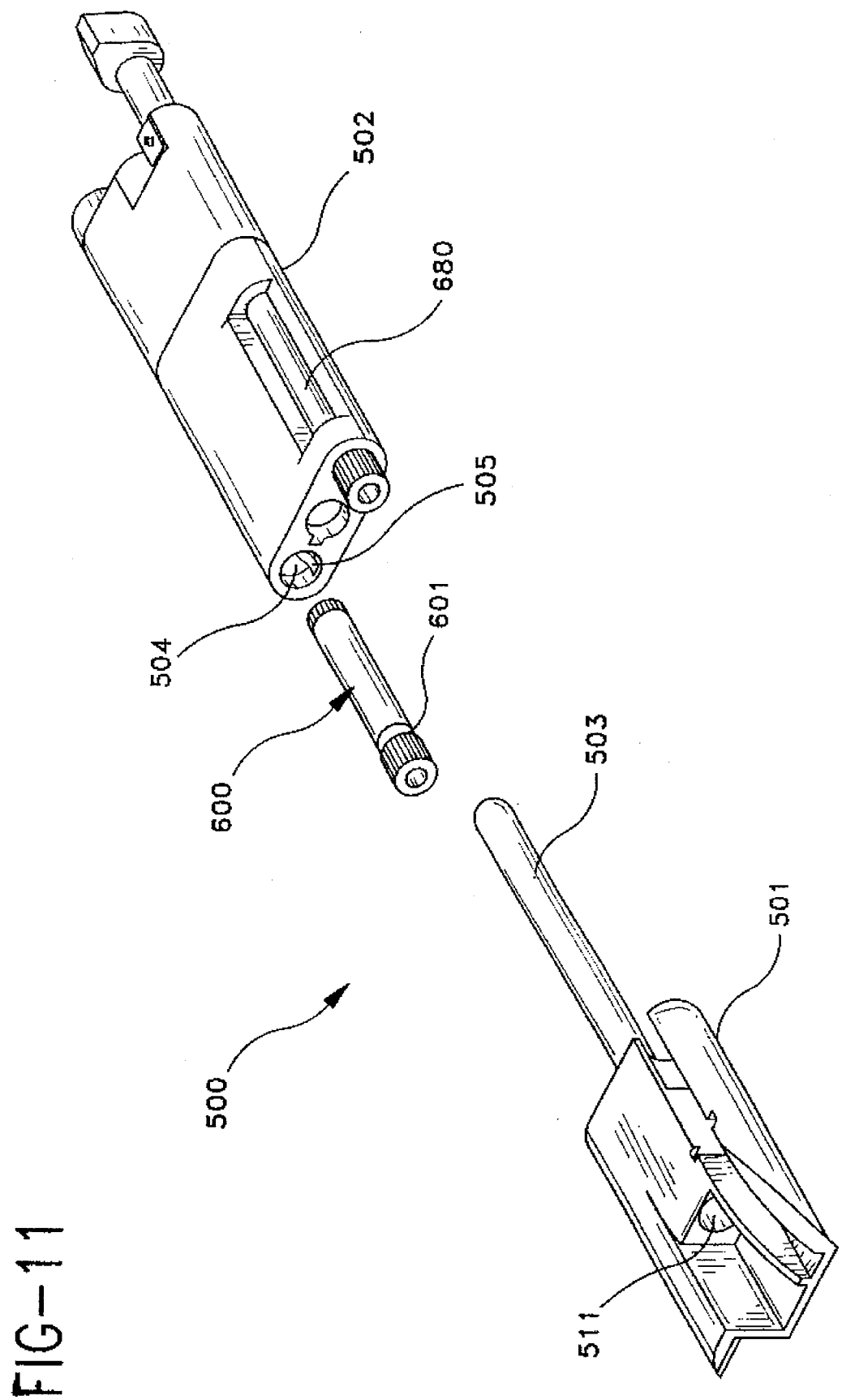

5,542,760

SYRINGE FILLER FOR MIXING INSULINS

BACKGROUND OF THE INVENTION

1. Field of the Invention

The subject invention relates to a device and method for filling a conventional disposable plastic syringe with a mixture of insulins.

2. Description of Related Art

Hypodermic syringes are used to deliver selected doses of medication to patients. The prior art hypodermic syringe includes a syringe barrel having opposed proximal and distal ends. A cylindrical chamber wall extends between the ends and defines a fluid receiving chamber. The proximal end of the prior art syringe barrel is substantially open and receives a plunger in sliding fluid fight engagement. The distal end of the prior art syringe barrel includes a passage communicating with the chamber. A needle cannula may be mounted to the distal end of the prior art syringe barrel, such that the lumen of the needle cannula communicates with the passage and the chamber of the syringe barrel. Movement of the plunger in a proximal direction draws fluid through the lumen of the needle cannula and into the chamber. Movement of the plunger in a proximal-to-distal direction urges fluid from the chamber and through the lumen of the needle cannula.

Medication to be injected with the prior art hypodermic syringe is commonly stored in a vial having a pierceable elastomeric seal and accessed by piercing the elastomeric seal with the needle cannula of the syringe. A selected dose of the medication is drawn into the chamber of the syringe barrel by moving the plunger of the syringe a selected distance in a proximal direction. The needle cannula is then withdrawn from the vial and the medication is injected into a patient by moving the plunger in a distal direction.

Some medication, such as insulin, is self-administered and a typical diabetes patient will require injections of insulin several times during the course of the day. The required dose of insulin will vary from patient to patient, and for each patient may vary during the course of the day and from day to day. Each diabetes patient will establish a regimen that is appropriate for his or her own medical condition and for his or her lifestyle. Sometimes the regimen will include some combination of a slow acting (Regular) insulin and an intermediate acting (NPH) insulin which may require the diabetes patient to periodically mix and/or self-administer insulin in public locations, such as places of employment or restaurants. The manipulation required to do this using the standard prior art hypodermic syringe and vial can be inconvenient and embarrassing in these public environments.

Normally, insulin "free-mixing" is performed with two 10 ml vials (not cartridges) of insulin sealed with a rubber septum. The first step involves adding a volume of air to each vial that is equal to the insulin volume to be removed. This is important to prevent an ever-increasing vacuum in the vial as insulin is removed. Next, a conventional disposable syringe is inserted in a NPH vial and the desired volume (units) is drawn up. If too much is drawn into the syringe, the excess can be returned to the NPH vial. The syringe is then inserted into a Regular vial and a mental calculation is made to determine the amount of draw since the target syringe scale is not reading the Regular insulin dose alone, but the sum of NPH and Regular. If too much Regular insulin is drawn into the syringe, the syringe contents must be totally discarded and the entire process restarted. The contents needs to be discarded since the syringe contains some NPH insulin which can not be returned to the Regular vial. Therefore, the above process is by no means easy to do and is also complicated by the fact that people with diabetes frequently have vision problems, manual dexterity problems or both.

Because of the difficulty in "free-mixing" with vials, physicians often prescribe a pre-mixture of the two types of insulin, which are combined by drug companies into one vial. However, pre-mixtures are infrequently made at the desired ratio for all patients and are not compatible with the frequent adjustments necessary for "tight" glycemic control. It is not possible to change the dose on one type of insulin without simultaneously changing the other insulin component in such a pre-mixture.

Medication delivery pens offer certain conveniences over syringes to the patient who is required to self-administer medication, i.e., less embarrassment. However, the insulin containing cartridges used in such pens are also not readily available in all the pre-mix ratios that are required by diabetic patients that must mix their insulin. Therefore, there is the need to provide a device and/or method that makes it easier for a diabetic patient to carry, mix and load a syringe with the mixed insulin when performing such injections.

SUMMARY OF THE INVENTION

The subject invention relates to a device and method for filling a conventional disposable syringe with a mixture of insulins. The mixing device receives two disposable medication cartridge assemblies, with each assembly containing a different type or speed insulin required by a diabetic patient requiring mixed insulin injections.

Each disposable medication cartridge assembly is an elongate generally cylindrical structure having opposed proximal and distal ends. The distal end of each disposable medication cartridge assembly includes a pierceable elastomeric seal that may be repeatedly and resealable pierced by a needle on the distal end of a syringe being filled with the mixed insulin. The proximal end of each disposable medication cartridge assembly is received by a respective dispensing mechanism in the mixing device. Each disposable medication cartridge assembly includes plunger means slidably disposed in fluid tight engagement therein to cause insulin to be dispensed therefrom. Initially, the plunger means is disposed in a proximal position within the medication cartridge assembly and is moved in a distal direction by a driver head projecting from the dispensing mechanism to dispense the insulin contained therein.

The mixing device includes two dispensing mechanism each having a lead screw with a driver head projecting from its distal end for selectively engaging the plunger in the respective disposable cartridge assembly and for urging the plunger of the disposable cartridge assembly in a distal direction. At least a portion of the lead screw includes driving threads engaged with other portions of the dispensing device that are operative to achieve axial movement of the lead screw in response to axial forces exerted on a rotatable actuator button at the proximal end of each dispensing mechanism. Each dispensing mechanism further comprises a dose setting means for establishing and precisely controlling the amount of medication to be delivered in response to each actuation of the actuator button.

The mixing device also includes a syringe holder assembly having a storage area for carrying a disposable syringe for use with the mixing device. The syringe holder assembly is rotatably and slidably mounted to the distal end of the housing of the mixing device to open and align the syringe with either disposable cartridge assembly during the mixing/dispensing operation.

The present invention provides a device and method that eliminates dialing errors since they can be easily corrected during the dose selection process, provides a procedure that is simplified since it requires less visual and manual dexterity, a device that is more compact and discreet for taking injections away from home, and a device that is as convenient as pre-mixing but provides the patient with the benefits of "free-mixing."

These and other aspects, features and advantages of the present invention will become apparent from the following detailed description taken in conjunction with the accompanying drawings.

DESCRIPTION OF THE DRAWINGS

FIG. 6 is a cross-sectional view of the device for mixing insulins along lines 6—6 shown in FIG. 1 in a preload position;

FIG. 7 is a cross-sectional view of the device for mixing insulins shown in FIG. 1 in a loaded position;

FIG. 9 is a cross-sectional view of the device for mixing insulins shown in FIG. 1 with the syringe in a storage area in the syringe holder assembly;

FIG. 10 is a cross-sectional view of the device for mixing insulins shown in FIG. 1 with a cartridge being loaded into position; and FIG. 11 is a exploded perspective view of an alternative embodiment of a device for mixing insulins according to the present invention.

DETAILED DESCRIPTION

Figure 1:
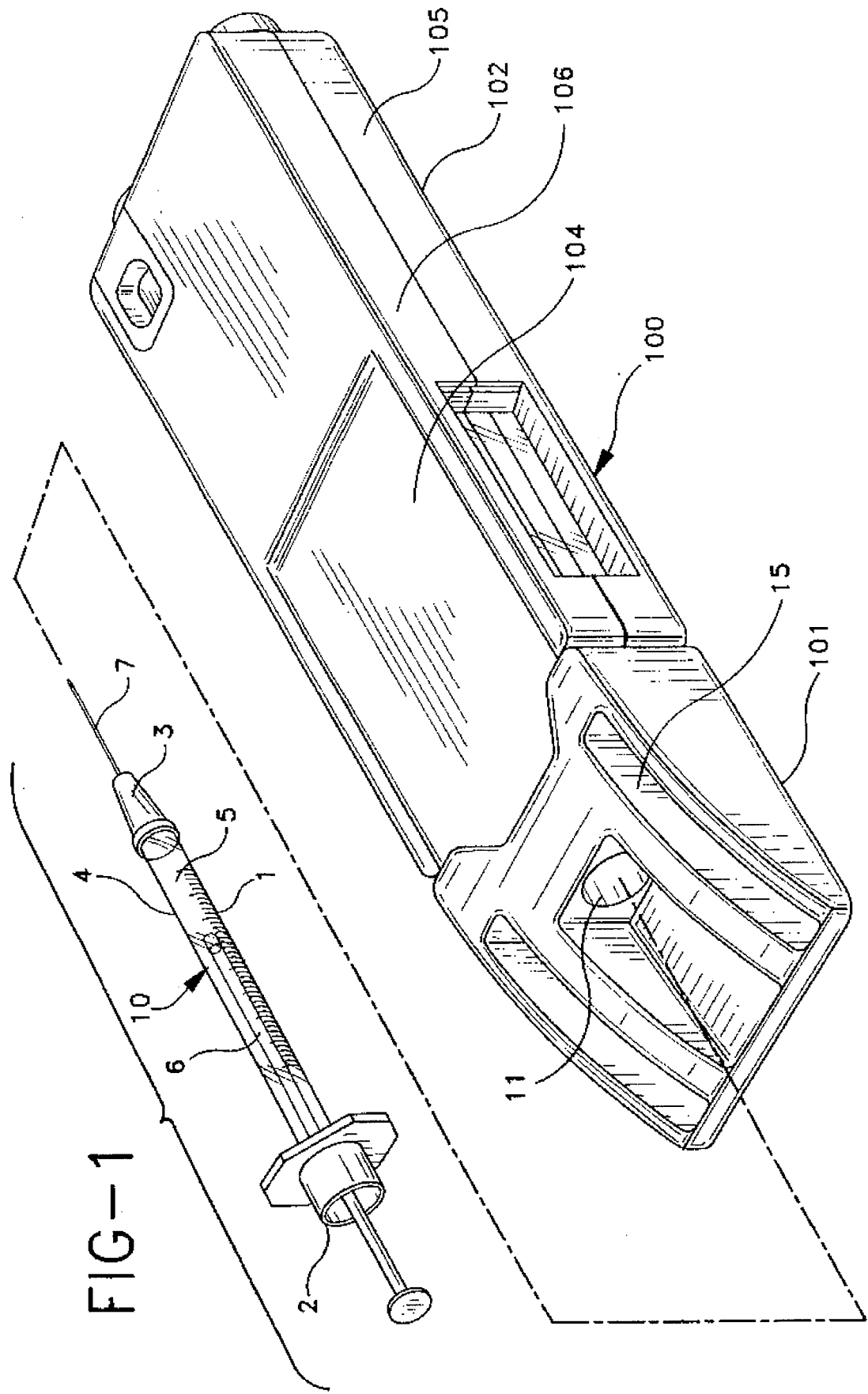
FIG. 1 is a perspective view of a syringe and a device for mixing insulins according the present invention.

FIG. 1 is a perspective view of a syringe 10 and a mixing device 100 for mixing insulins according to the present invention. As shown in FIG. 1, mixing device 100 includes a syringe holder assembly 101 rotatably and slidably mounted on a housing 102. Syringe holder assembly 101 includes a storage area 11 for receiving syringe 10 when syringe 10 is transported with mixing device 100 prior to use. Housing 102 includes lower shell 105 and an upper shell 106 with a door 104 located in upper shell 106 that provides means for the patient to load and unload disposable medication cartridge assemblies therefrom. Housing 102 also includes two dispensing mechanisms, shown in FIGS. 4 and 5, that interact with respective disposable medication cartridge assemblies to fill syringe 10 with mixed insulin, as described further below.

Syringe 10 is a conventional disposable syringe having a syringe barrel 1 with opposed proximal and distal ends 2 and 3, respectively. A cylindrical chamber wall 4 extends between the ends and defines a fluid receiving chamber 5. Proximal end 2 of syringe barrel 1 is substantially open and receives a plunger 6 in sliding fluid fight engagement. Distal end 3 of syringe barrel 1 includes a needle cannula 7 mounted thereto such that a lumen in needle cannula 7 communicates with chamber 5 in syringe barrel 1. Movement of plunger 6 in a proximal direction draws fluid through the lumen of needle cannula 7 and into chamber 5. While movement of plunger 6 in a proximal-to-distal direction urges fluid from chamber 5 and through the lumen of needle cannula 7.

Figure 2:
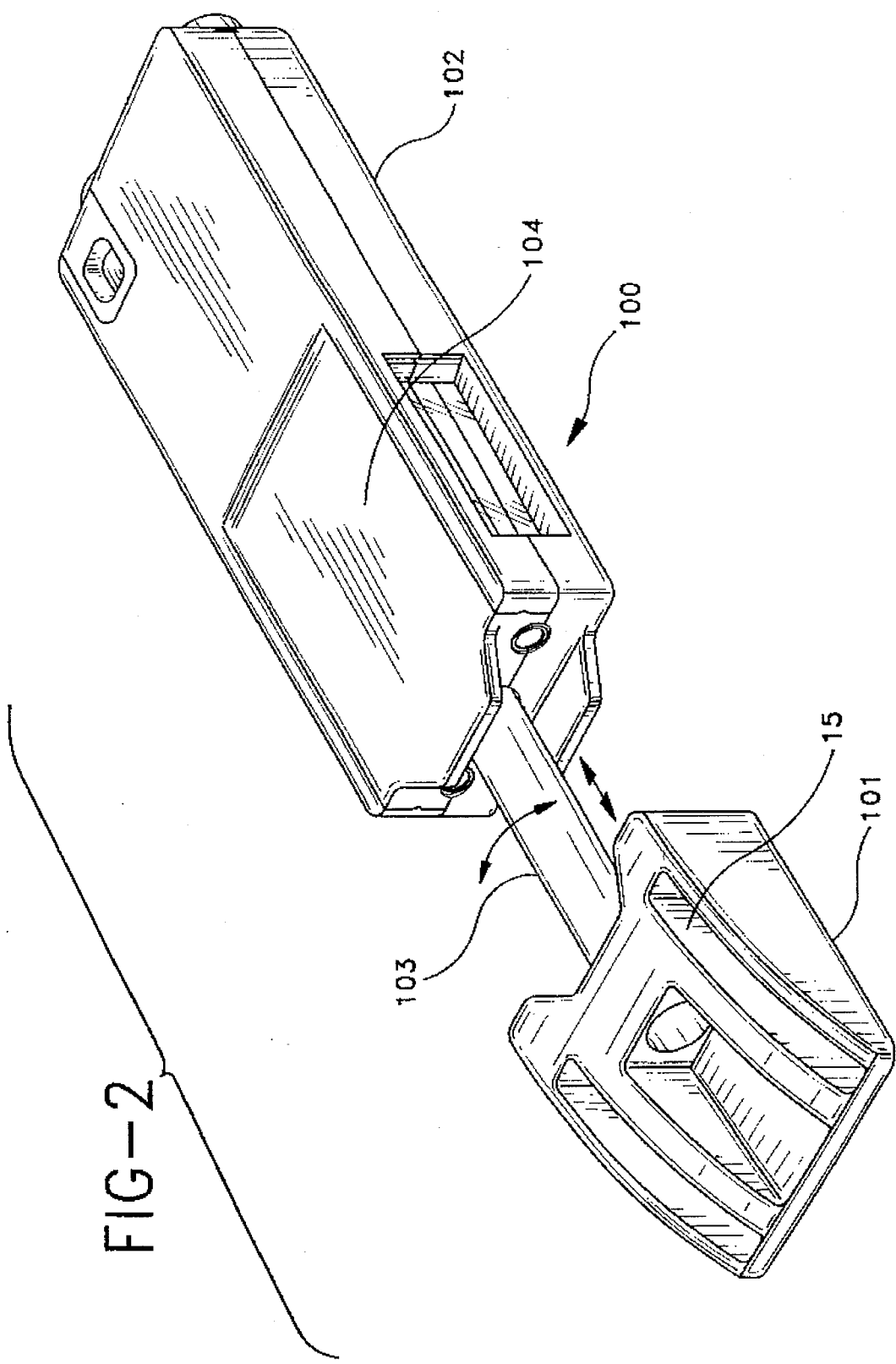
FIG. 2 is a perspective view of the device for mixing insulins shown in FIG. 1 with a syringe holder assembly in an open position.
Figure 3:
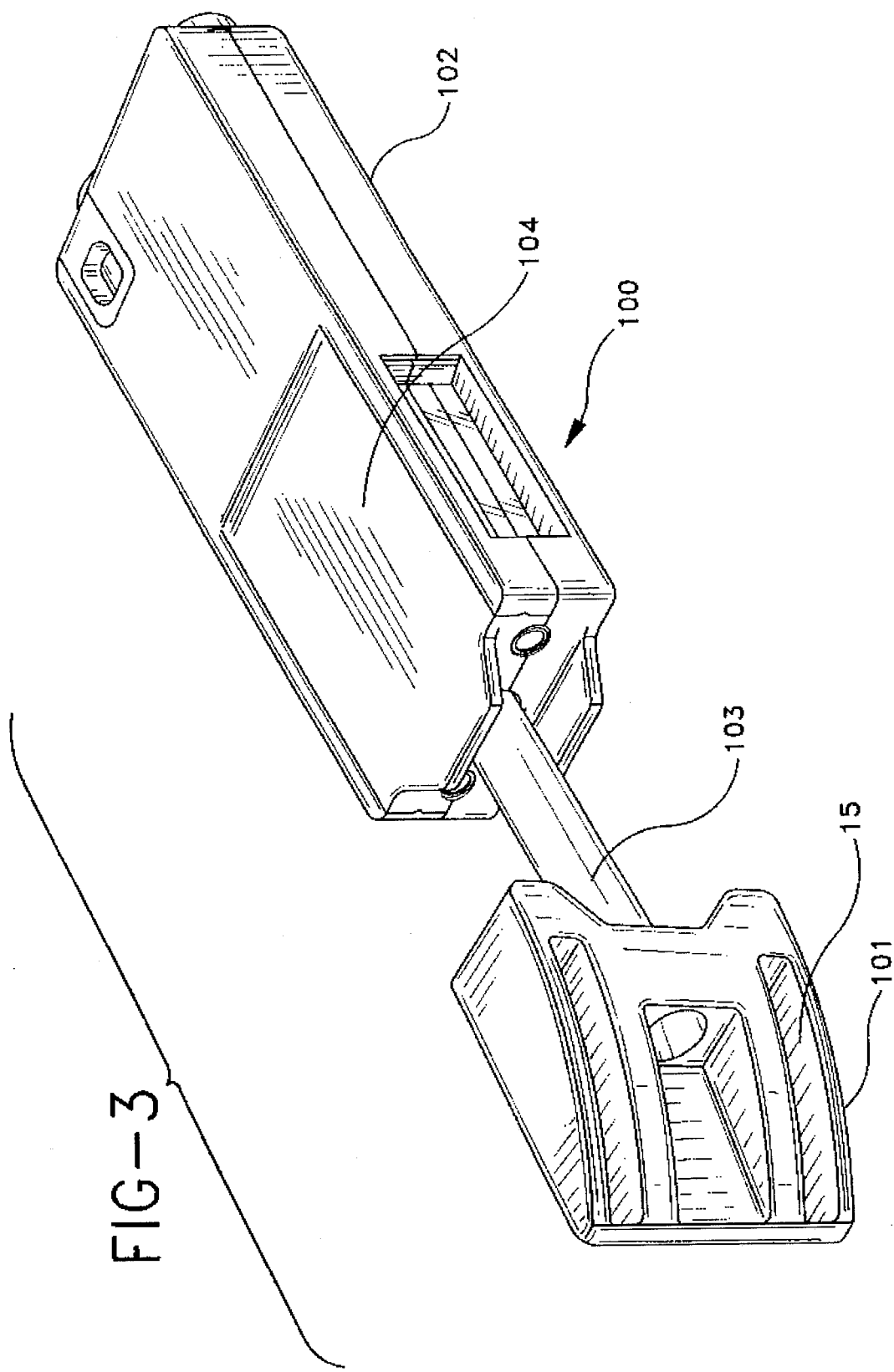
FIG. 3 is a perspective view of the device for mixing insulins shown in FIG. 1 with the syringe holder assembly in a rotated position.

FIGS. 2 and 3 are perspective views of mixing device 100 with syringe holder assembly 101 in an open position and a rotated position, respectively. As shown in FIGS. 2 and 3, syringe holder assembly 101 is rotatably attached to housing 102 by a sliding shaft 103 that allows syringe holder assembly 101 to slide from a closed position in FIG. 1 to a first open position in FIG. 2. Shaft 103 also allows syringe holder assembly 101 to rotate from the first open position in FIG. 2 to the rotated position in FIG. 3. Syringe holder assembly 101 is also free to rotate from the rotated position in FIG. 3 to a second open position wherein syringe holder assembly is inverted with respect to its position in FIG. 2. When syringe holder assembly 101 is in the first open position mixing device 100 is in position to begin a filling operation from a first dispensing mechanism and when syringe holder assembly 101 is in the second open position it is in position to begin the filling operation from a second dispensing mechanism.

The preferred embodiment of mixing device 100 is illustrated in greater detail in FIGS. 4–10. It is understood, however, that variations from this preferred embodiment may be provided, and are considered to be within the scope of the subject invention.

Figure 4:
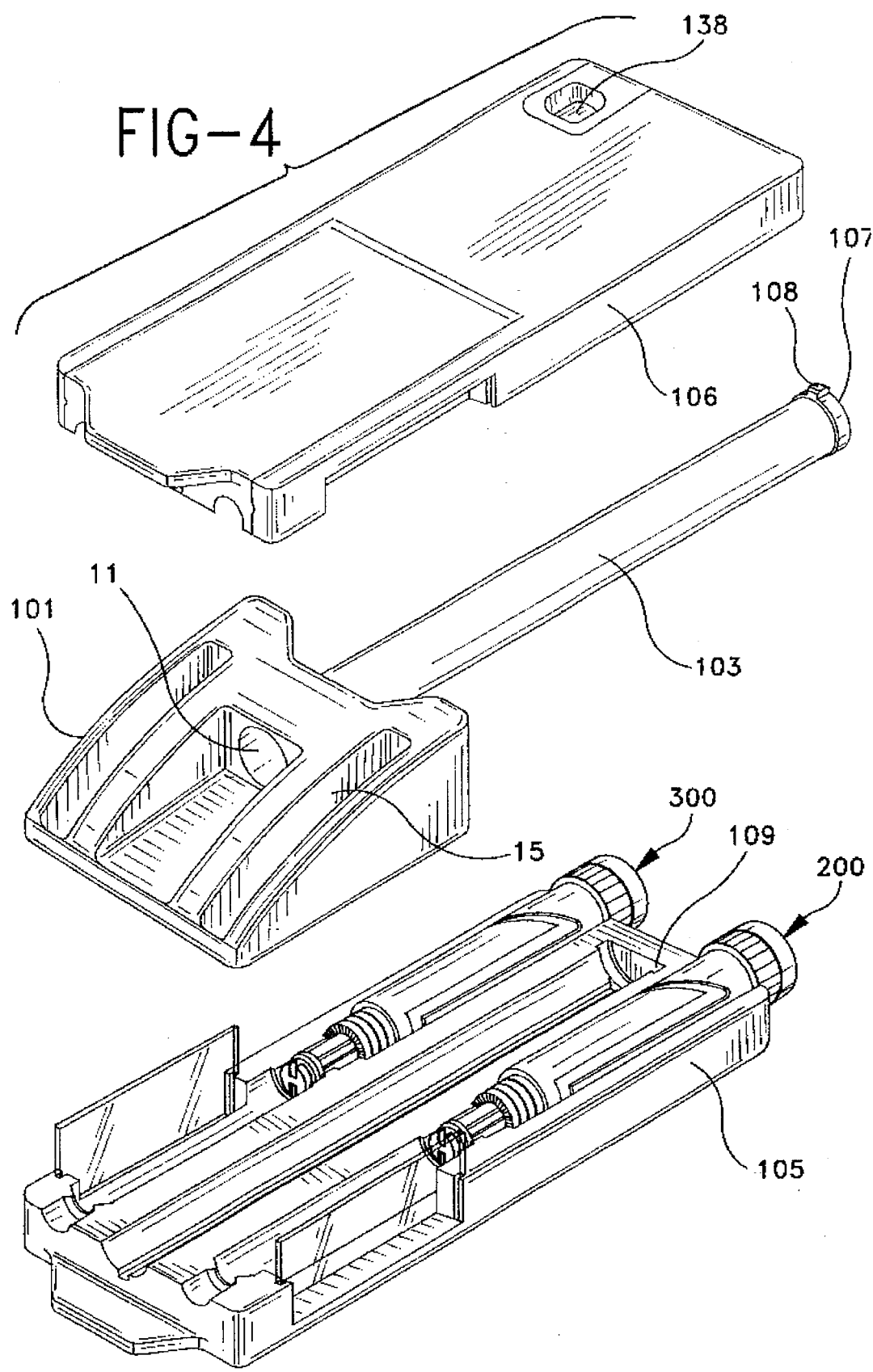
FIG. 4 is an exploded perspective view of the device for mixing insulins shown in FIG. 1.
Figure 5:
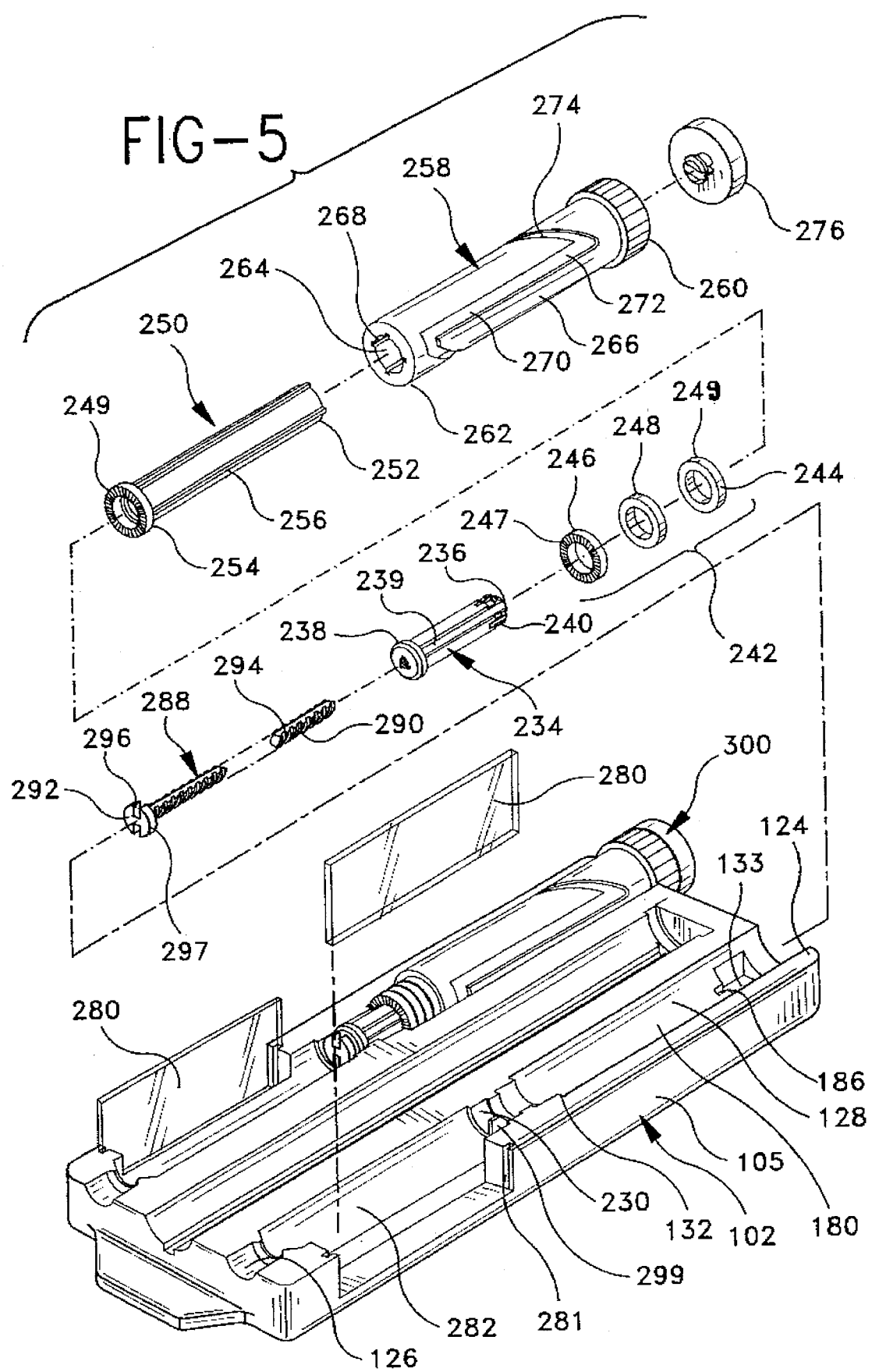
FIG. 5 is another exploded perspective view of the device for mixing insulins shown in FIG. 1.

FIGS. 4 and 5 show exploded perspective views of mixing device 100. FIG. 4 shows housing 102 with upper shell 106 removed to reveal syringe holder assembly 101 and first and second dispensing mechanisms 200 and 300, respectively.

FIG. 5 is a more exploded view than FIG. 4 to show the details of first dispensing mechanism 200. It should be appreciated that dispensing mechanism 300 is identical to dispensing mechanism 200 and will therefore not be described in detail. As shown in FIG. 5, upper shell 106 and lower shell 105 when attached together form two generally cylindrical chambers 128 within housing 102, with each chamber 128 having opposed proximal and distal ends 124 and 126. A portion of each cylindrical chamber 128 in housing 102 adjacent distal end 126 is characterized by an array of clutch teeth 132 molded therein. Proximal end 124 of housing 22 is characterized by a pair of windows 133 and 138, as shown in FIGS. 4 and 5, respectively.

Dispensing mechanism 200 includes a nut 234 having opposed proximal and distal ends 236 and 238 respectively. Exterior surface regions of nut 234 between proximal and distal ends 236 and 238, shown in FIG. 4, define a plurality of longitudinally extending splines 239. Proximal end 236 of nut 234 is characterized by a plurality of longitudinally extending resilient fingers 240 with enlarged ends that enable snap engagement of nut 234 into other portions of dispensing mechanism 200, as explained further herein. Distal end 238 of nut 234 is radially enlarged to fit in a collar 230 and limit axial movement of nut 234 in chamber 128. However, the dimensions and configurations of nut 234 and collar 230 in chamber 128 permit free relative rotation there between.

Dispensing mechanism 200 further includes a clutch assembly 242 mounted therein. Clutch assembly 242 includes a proximal clutch 244, a distal clutch 246 and an annular spring 248 biasingly engaged there between. Proximal and distal clutches 244 and 246 each are configured for non-rotatable engagement over splines 239 of nut 234. Distal clutch 246 includes an array of distally facing saw teeth 247 dimensioned, disposed and configured for engagement with teeth 132 on the interior of housing 102, such that distal clutch 246 can rotate only in one direction relative to housing 102. Proximal clutch 244 includes an array of proximally facing teeth 241 which are also configured for unidirectional rotation as explained further herein.

Dispensing mechanism 200 further includes a generally cylindrical driver 250 having opposed proximal and distal ends 252 and 254. Driver 250 is slidably receives nut 234, such that distal end 254 of driver 250 is snap fit over the enlarged ends of resilient fingers 240 at proximal end 236 of nut 234. This snap fit engagement prevents axial movement between nut 234 and driver 250, but permits free relative rotational movement within chamber 128. Distal end 254 of driver 250 is also characterized by an array of saw teeth 249 that engage with saw teeth 241 on proximal clutch 244. Outer surface regions of driver 250 are characterized by splines 256 extending radially outwardly thereon and along a substantial portion of the length of driver 250.

Dispensing mechanism 200 further includes a dose knob 258 which is a hollow generally cylindrical structure having opposed proximal and distal ends 260 and 262 and opposed inner and outer surfaces 264 and 266. Inner surface 264 is characterized by longitudinally extending grooves 268 which are disposed and dimensioned for engagement with splines 256 on driver 250. More particularly, dose knob 258 is spline mounted over driver 250 so that axially extending grooves 268 in dose knob 258 engage splines 256 of driver 250 to prevent relative rotation there between, but permitting relative axial movement in chamber 128. Outer surface 266 of dose knob 258 is characterized by a groove 270 that includes a linear component 272 and a helical component 274, which connects opposed ends of linear component 272. Portions of outer surface 266 adjacent helical component 274 of groove 270 are provided with dosage indicia to define dose amounts corresponding to different positions along groove 270 as explained further herein. Proximal end 260 of dose knob 258 is characterized by a gnarled exterior surface to facilitate manipulation for setting a selected dose. An actuator button 276 is snapped in to engagement with proximal end 260 of dose knob 258 to permit relative rotation there between.

An inner surface 180 of chamber 128 includes a button 186 dimensioned and disposed to engage in groove 270 of dose knob 58. Button 186 and window 133 are disposed to enable the indicia on dose knob 258 to be visible through window 133 as dose knob 258 is rotated and button 186 travels along groove 270.

Dispensing mechanism 200 further includes a lead screw 288 with opposed proximal and distal ends 290 and 292 and an array of external threads 294. External threads 294 are characterized, however, by a pair of opposed axially extending grooves 296 which extend from distal end 292 substantially to the proximal end 290. Threads 294 are engaged in nut 234, such that proximal end 290 of lead screw 288 is within chamber 128 and a driver head 297 at distal end 292 projects distally beyond collar 230.

Dispensing mechanism 200 is assembled by sliding clutch assembly 242 over splines 239 on nut 234. Driver 250 is then sufficiently urged onto nut 234 in a distal direction for snap fit engagement with nut 234. In this snapped engagement, saw teeth 241 of proximal clutch 244 will be engaged with saw teeth 249 at distal end 254 of driver 250. Spring 248 will maintain constant selected pressure between these interengaged saw teeth. Dose knob 258 is then slid onto driver 250, an actuator button 276 is snapped into engagement with proximal end 260 of dose knob 258, and lead screw 288 is threaded into nut 234. Assembled dispensing mechanisms 200 and 300 are then inserted into their respective chamber 128 in lower shell 105 such that their respective groove 270 in dose knob 258 receives their respective button 186. When each dispensing mechanism 200 and 300 are inserted into their respective chamber 128, groove 296 on lead screw 288 receives an anti-rotation tab 299 extending from chamber 128 near collar 230. Anti-rotation tabs 299 is dimensioned to slidably engaged in groove 296 on lead screw 288 so that lead screw 288 can slidably move relative to antirotation tab 299 but is prevented from rotating relative to tab 299.

Dispensing mechanism 200 further includes a pair of windows 280 located in a window receiving area 281 on each side of housing 102. Each window 280 provides visual access to a disposable medication cartridge assembly holding area 282 near the distal end of chamber 128. A disposable medication cartridge assembly 400 is loaded into holding area 282 prior to using mixing device 100 by opening door 104, as shown in FIG. 10 removing any empty cartridge assembly 400 therein and pushing lead screw 288 in a proximal direction back into dispensing mechanism 200. After lead screw 288 has been replaced in dispensing mechanism 200 a new disposal medication cartridge assembly 400 can be loaded into holding area 282. Door 104 is then closed and lead screw 288 is moved forward using dispensing mechanism 200 until distal end 292 of lead screw 288 engages plunger 418 and cartridge assembly 400, as shown in FIG. 6. Of course, a medication cartridge assembly 400 containing a different type of insulin needed for mixing is installed in the other side of housing 102 corresponding to dispensing mechanism 300 prior to closing door 104 if that medication cartridge assembly requires replacing.

The newly loaded mixing device 100 may then be stored until a selected mixed dose of medication is required. Just prior to use, syringe 10 is removed from storage area 11 and mounted in syringe loading area 15 in syringe holder assembly 101 when mixing device is in the closed position shown in FIG. 1. This operation causes cannula 7 of syringe 10 to pierce pierceable elastomeric seal 411 of medication cartridge assembly 400, as shown in FIG. 6, and provide communication with medication 420.

Figure 8:
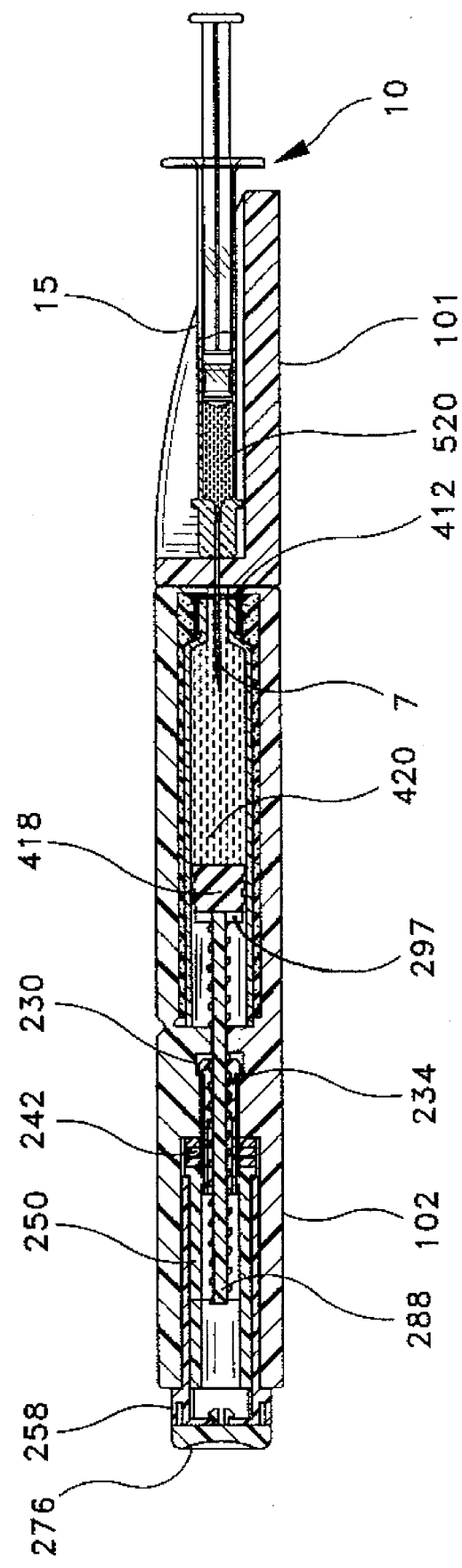
FIG. 8 is a cross-sectional view of the device for mixing insulins shown in FIG. 1 in a dispensed position.

FIGS. 6–8 are cross-sectional views of mixing device 100 showing the operation of using one dispensing mechanism 200 to fill syringe 10 with one type of insulin. FIG. 6 shows mixing device 100 in a preload position, wherein cannula 7 on syringe 10 has been inserted through pierceable elastomeric seal 411 into disposable medication cartridge assembly 400.

As shown in FIG. 6, each medication cartridge assembly 400 is securely retained in holding area 282 of housing 102. Medication cartridge assembly 400 includes an open proximal end 410 and a distal end 412 having a pierceable elastomeric seal 411 securely mounted thereto. A plunger 418 is disposed in sliding fluid fight engagement in medication cartridge assembly 400. Plunger 118 initially is disposed substantially adjacent proximal end 410 of medication cartridge assembly 400. Portions of medication cartridge assembly 400 between plunger 418 and seal 411 are filled with medication 420, such as insulin.

After a dosage has been set using dose knob 258, mixing device 100 and syringe 10 are in the loaded position, shown in FIG. 7. In the loaded position, a desired dose of medication 420 has been set by rotating dose knob 258 until indicia corresponding to the desired dose of that type of medication appears in window 133. At this position button 186 in chamber 128 has traveled in helical portion 274 of groove 270 in dose knob 258 to cause a threaded retraction of dose knob 258 relative to driver 250. This threaded retraction of dose knob 258 causes simultaneous rotation of driver 250 that is splined thereto, but nut 234 does not rotate because saw teeth 247 on distal clutch 246 and saw teeth 132 on interior portions of chamber 128 are locked to prevent rotation in that direction. Proximal clutch 244 is splined to nut 234 and hence also will not turn. However, saw teeth 249 at distal end 254 of driver 250 are shaped to allow rotation relative to proximal clutch 244, and will provide an audible click for each unit of medication in the selected dose. This is helpful for visually impaired patients who may be required to set mixed dosages themselves. Annular spring 248 contributes to the engagement that provides these audible clicking sounds.

When the desired dose is set, as shown in FIG. 7, dispensing is achieved by merely pushing on actuator button 276. After the insulin has been dispensed from dispensing mechanism 200 into syringe 10, mixing device 100 and syringe 10 are in a dispensed position, shown in FIG. 8. In the dispensed position, dose knob 258 has been turned about helical groove 274 relative to chamber 128, and driver 250 has rotated through the same number of degrees. This rotation is opposite to the rotation generated during dose setting using dose knob 258, and the rotational freedom of clutch assembly 242 is reversed. Therefore, as driver 250 turns previously clicking proximal clutch 244 is locked to and turns with driver 250. This driving movement of proximal clutch 244 causes the corresponding rotational movement of nut 234 because of the splined engagement therebetween. Distal clutch 246 is now free to rotate against saw teeth 132 in chamber 128 and make an audible clicking indication during dispensing of the medication. During dispensing, rotation of lead screw 288 is prevented by tab 299 in collar 230. Therefore, as nut 234 rotates under the driving action of proximal clutch 244 in driver 250, lead screw 288 will be advanced actually into medication cartridge assembly 400. This axial advancement of lead screw 88 causes distal end 292 thereof to urge plunger 418 distally into cartridge 400 and hence cause medication 420 to be dispensed through cannula 7 into syringe chamber 5. Dispensing will be terminated when dose knob 258 engages proximal end 124 of housing 102, as shown in FIG. 8. FIG. 8 also shows medication 520 contained in syringe 10 because of the dispensing operation.

Upon completion of dispensing medication from dispensing mechanism 200, syringe holder assembly 101 is slid away from housing 102 to the opened position shown in FIG. 2. Syringe holder assembly 101 is then rotated past the rotated position shown in FIG. 3 to a second opened position, wherein syringe holder assembly 101 is inverted with respect to the position it had in FIG. 2 and is ready for closing and insertion of cannula 7 into the cartridge assembly corresponding to dispensing mechanism 300. The same operation that took place with dispensing mechanism 200 is now repeated for dispensing mechanism 300 to dispense the different type of insulin into syringe 10 and complete the medication mixing process. Upon completion of the second dispensing operation, the patient removes syringe 10 from syringe filling area 15 and performs the necessary mixed medication injection. After injection syringe 10 is properly disposed of, a new disposable syringe 10 can be inserted into storage area 11 for the next mixed medication injection. Mixing device 100 can therefore be used repeatedly until one of the medication cartridges become empty and needs to be replaced, as shown in FIG. 10.

FIG. 9 is a cross-sectional view of mixing device 100 with syringe 10 located in syringe storage area 11. When syringe 10 is in the stored position, mixing device 100 and syringe 10 can be easily transported by the patient until it is time for the next mixed injection. At that time the patient removes syringe 10 from syringe storage area 11 and performs the mixing method set forth above. As shown in FIG. 9, cannula 7 is retained in storage area 11 to prevent contamination prior to use by the patient. FIG. 10 is a cross-sectional view of mixing device 100 with door 104 in an open position. With door 104 open, the patient can remove and replace each disposable medication cartridge assembly 400 with new cartridge assemblies containing the type of insulin required by the patient to perform insulin mixing.

FIG. 11 is a exploded perspective view of an alternative embodiment of a mixing device 500 for mixing insulins according to the present invention. Mixing device 500 is very similar to mixing device 100 discussed above and includes a housing 502 and a rotatable syringe storage device 501 having a syringe storage area 511. However, mixing device 500 includes an alternative means for inserting and retaining each disposable medication cartridge assembly 600 within housing 502. As shown in FIG. 11, cartridge assembly 600 includes a tab 601 extending from an outer wall near its distal end that is received in a threaded slot 505 when cartridge assembly 600 is inserted into a corresponding cartridge chamber 504. Tab 601 interacts with slot 505 in a bayonet fashion to hold cartridge assembly 600 in cartridge chamber 504. Alternatively, cartridge assembly 600 could include threads that mate with corresponding threads near the opening of cartridge chamber 504 to retain cartridge assembly 600 in housing 502. Both of the mechanism replace door 104 in mixing device 100, described above, for loading and unloading a cartridge assembly in the device.

While the invention has been described with respect to a preferred embodiment, it is apparent that various changes can be made without departing from the scope of the invention as defined by the appended claims. In particular, the dispensing mechanism may have other driving and/or clutch mechanisms. Additionally, different means for preventing and/or enabling rotation during the dose setting and dispensing phases may be provided. Similarly, other means for loading and unloading cartridge assemblies in the mixing device may be provided. These various optional constructions will be apparent to those skilled in the art after having read the subject disclosure.

What is claimed is:

1. A mixing device for filling a syringe having a cannula with a mixture of medication, said mixing device comprising:

a housing;

a pair of disposable medication-containing cartridges in said housing, each cartridge having a pierceably sealed distal end, an open proximal end and a plunger in sliding fluid tight engagement within said cartridge;

a pair of dispensing mechanisms in said housing having opposed proximal and distal ends with each dispensing mechanism corresponding to one of said pair of disposable medication-containing cartridges for dispensing the medication contained therein;

means rotatably mounted to said housing for positioning a cannula of a syringe to be filled with a mixture of medication for insertion into one of said pair of disposable medication-containing cartridges containing a first medication and then the other of said pair of disposable medication-containing cartridges containing a second medication; and each of said dispensing mechanisms further comprising:
  a lead screw having a distal end projecting beyond said distal end of said dispensing mechanism for selective engagement with said plunger and a plurality of threads extending between said proximal end and said distal end of said lead screw;
  dose setting means for defining specified distances of travel for said lead screw corresponding to selected doses of medication to be dispensed; and
  driver means for moving said lead screw distally into said respective disposable medication-containing cartridge said distance specified by said dose setting means to dispense the selected dose of medication from said medication-containing cartridge through said cannula into said syringe.

2. The mixing device of claim 1, wherein said dispensing mechanism further includes an actuator button rotatably mounted on said driver means, such that axial forces exerted on said actuator button generates movement of said lead screw distally into said cartridge assembly.

3. The mixing device of claim 1, wherein said lead screw includes at least one anti-rotation groove extending axially therealong and said dispensing mechanism further includes tab means for slidably engaging in said anti-rotation groove of said lead screw for preventing relative rotation between said lead screw and said dispensing mechanism.

4. The mixing device of claim 1, wherein the means for positioning the cannula of the syringe comprises a syringe holder assembly that is rotatably attached to said housing by a sliding shaft that allows said syringe holder assembly to rotate and position the cannula for insertion into the respective medication-containing cartridge.

5. The mixing device of claim 4, wherein said syringe holder assembly includes a storage area for storing a syringe to be filled and a syringe loading area that can be aligned with either disposable medication-containing cartridge when syringe holder assembly has been rotated into position.

6. The mixing device of claim 1, wherein each disposable medication-containing cartridge contains a different type of medication.

7. The mixing device of claim 6, wherein the medication in each disposable medication-containing cartridge is insulin.

8. A method for filling a conventional disposable plastic syringe having a cannula with a mixture of medications using a mixing device having a syringe holder assembly rotatably mounted on a housing including a first and second disposable cartridge assembly each containing a different type of medication and a first and second medication dispensing mechanism for dispensing the medication out of each respective cartridge assembly, said method comprising the steps of:

inserting a cannula of a syringe into a syringe loading area in a syringe holder assembly rotatably mounted on a housing;

moving the syringe holder assembly to a first opened position and then closing the syringe holder assembly to cause the cannula to enter a first disposable cartridge assembly;

setting a first dose amount of a first medication on a first medication dispensing mechanism in the housing;

dispensing the first dose amount from the first disposable cartridge assembly into the syringe using the first medication dispensing mechanism;

moving the syringe holder assembly to a second opened position and then closing the syringe holder assembly to cause the cannula to enter a second disposable cartridge assembly;

setting a second dose amount of a second medication on a second medication dispensing mechanism in the housing;

dispensing the second dose amount from the second disposable cartridge assembly into the syringe using the second medication dispensing mechanism; and removing the syringe containing the mixed medication from the syringe loading area.

* * * * *